United States Patent
Holmes

(10) Patent No.: US 9,528,983 B2
(45) Date of Patent: Dec. 27, 2016

(54) PHYSICOCHEMICAL MODIFICATION AND APPLICATION OF ALGINATE GELS FOR THE CONTROLLED RELEASE OF REAGENTS IN CLASSICAL SOLUTION ASSAYS AND MICROFLUIDIC ASSAYS

(71) Applicant: Anna Merritt Holmes, Madison, AL (US)

(72) Inventor: Anna Merritt Holmes, Madison, AL (US)

( * ) Notice: Subject to any disclaimer, the term of this patent is extended or adjusted under 35 U.S.C. 154(b) by 0 days.

(21) Appl. No.: 14/710,567

(22) Filed: May 12, 2015

(65) Prior Publication Data

US 2015/0323522 A1 Nov. 12, 2015

Related U.S. Application Data

(60) Provisional application No. 61/992,119, filed on May 12, 2014, provisional application No. 62/022,519, filed on Jul. 9, 2014.

(51) Int. Cl.
| | | |
|---|---|---|
| *G01N 33/52* | (2006.01) | |
| *A61K 9/00* | (2006.01) | |
| *C12Q 1/527* | (2006.01) | |
| *A61K 9/48* | (2006.01) | |
| *A61K 9/50* | (2006.01) | |
| *A61K 35/12* | (2015.01) | |
| *A61K 9/16* | (2006.01) | |
| *A61K 9/51* | (2006.01) | |

(52) U.S. Cl.
CPC ............... *G01N 33/52* (2013.01); *C12Q 1/527* (2013.01); *G01N 33/525* (2013.01); *A61K 9/1652* (2013.01); *A61K 9/4891* (2013.01); *A61K 9/5036* (2013.01); *A61K 9/5161* (2013.01); *A61K 2035/128* (2013.01); *C12N 2533/74* (2013.01)

(58) Field of Classification Search
CPC .. A61K 9/1652; A61K 9/4891; A61K 9/5036; A61K 2035/128; A61K 9/5161; C12N 2533/74
See application file for complete search history.

(56) References Cited

U.S. PATENT DOCUMENTS

| | | | | |
|---|---|---|---|---|
| 2005/0067726 | A1* | 3/2005 | Yan | A23L 1/0029 264/4.1 |
| 2007/0134493 | A1* | 6/2007 | Meghpara | A61J 3/07 428/402.2 |
| 2010/0185146 | A1* | 7/2010 | Ramzipoor | A61M 25/10 604/103.02 |
| 2011/0104218 | A1* | 5/2011 | Karles | A23L 1/0029 424/401 |
| 2012/0071865 | A1* | 3/2012 | Jarrett | A61K 9/0048 606/4 |
| 2014/0105974 | A1* | 4/2014 | Weber | A61K 47/48869 424/463 |
| 2014/0127308 | A1* | 5/2014 | Opara | A61K 31/565 424/497 |
| 2014/0274970 | A1* | 9/2014 | Chandran | A61K 31/65 514/152 |

* cited by examiner

*Primary Examiner* — Jennifer Wecker
(74) *Attorney, Agent, or Firm* — Ann I. Dennen

(57) ABSTRACT

A reagent assay in accordance with the present disclosure has a porous alginate core containing a first reagent, a first polysaccharide layer coating the alginate core and having a second reagent, and at least one polysaccharide core comprising a hydration seal and coating the first polysaccharide layer.

36 Claims, 6 Drawing Sheets

PHYSICOCHEMICAL MODIFICATION AND APPLICATION OF ALGINATE GELS FOR THE CONTROLLED RELEASE OF REAGENTS IN CLASSICAL SOLUTION ASSAYS AND MICROFLUIDIC ASSAYS

CROSS-REFERENCE TO RELATED APPLICATIONS

This application claims priority to U.S. Provisional Patent Application Ser. No. 61/992,119 entitled Reagent Assay System filed on May 12, 2014 and to U.S. Provisional Patent Application Ser. No. 62/022,519 entitled Liquid Gellation [LIQ-GEL] Method to Enable Collection, Storage and Assay of Reagents or Analytes, filed on Jul. 9, 2014, both of which are incorporated herein by reference.

BACKGROUND

Alginate is an anionic polysaccharide harvested globally from eleven brown seaweeds. The North American variety *Macrocystis pyrifera* (giant kelp) and other varieties are found spanning the globe in both the northern and southern hemispheres, with the only cultivar, *Saccharina japonica* being developed in China, Japan, Russia, France and Korea. In industry, alginate applications of economic importance are in the fields of: dentistry (dental impressions), in the paint industry (plasticizers), in the food industry (as thickeners) and in the field of pharmacopeia (as compounding agents for tablets, capsules and as active ingredients in upset stomach preparations). It is also used extensively in burn trauma units as a protective dressing that requires no adhesive and subsequently is less painful for the burn patient on removal. It has also most recently gained fame in the theatrical and television industry when used by prosthetic makeup artists in the creation and modification of science fiction characters and masks.

Alginate hydrogel contains a co-polymer of β-D-mannuronate (M) and its C-5 epimer α-L-guluronate (G) that form a mixture of homopolymer consecutive blocks (M or G) or alternating blocks (M-G-M-G- . . . ) or unequal mixtures of these blocks (M-M-G-M-G-G-M . . . ) may occur and is based upon the prevalence of each co-polymer within the seaweed itself. An example representation of the structure of co-polymer components of alginate is shown with reference to FIG. 1

As an example, variation occurs in the M to G ratio (M:G) based on the turbulence of the waters whence the brown seaweed was harvested. In turbulent waters greater flexibility and higher strength of the seaweed (higher M content) is needed to maintain anchorage by a strong holdfast (analogous to a root in plants) and flexible stipe (analogous to a stem) as compared to a tidal pool that is sheltered. In this circumstance, the stipe may require more structure (higher G content) to enable the blade (analogous to leaves in plants) to rise above the water surface enabling successful competition against green algal mats that often cover the water surface.

Other modifying factors are the temperature and the depth of the waters from where it was harvested, the age of the kelp and whether they harvested the entire kelp holdfast, stipe or blade or only a portion (e.g.: the blade). In each case, the living kelp produces the appropriate M:G ratio to maintain its ecosystem. In some cases an algal kelp forest may include other kelp species that are harvested unintentionally (some giant kelp forests include 20 other species that are largely undisturbed when only the giant kelp blade is harvested). These factors promote variation from one alginate product lot to the next and therefore a small and simple test is required to select the appropriate ionic strength concentration (salts of sodium, potassium and calcium) for creating the desired porosity. From that point forward, constancy of formulation within the lot remains the same. This is a common practice in most biological reagents as the "activity of enzymes" changes with each lot. Alginates are available and sold in United States Pharmacopeia (USP) grade that requires sufficient purity to meet or exceed that used for food, drug or medicinal use.

SUMMARY

A reagent assay in accordance with the present disclosure has a porous alginate core containing a first reagent, a first polysaccharide layer coating the alginate core and having a second reagent, and at least one polysaccharide core comprising a hydration seal and coating the first polysaccharide layer.

BRIEF DESCRIPTION OF THE DRAWINGS

The various embodiments of the present disclosure are best understood by referring to FIGS. 1 through 6 of the drawings. The elements of the drawings are not necessarily to scale, emphasis instead being placed upon clearly illustrating the principles of the disclosure. Throughout the drawings, like numerals are used for like and corresponding parts of the various drawings.

DETAILED DESCRIPTION

Figure 1:
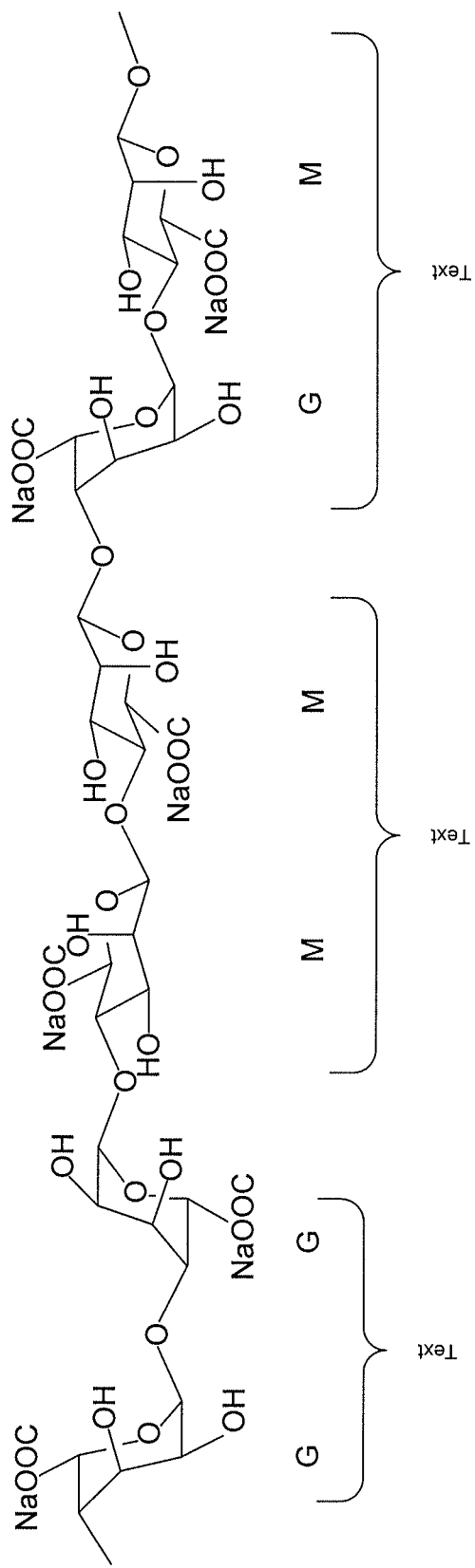
FIG. 1 is a representation of the molecular make-up of alginate.

The present disclosure describes a composition of a porous alginate and method of chemically modifying the porosity and conductivity of alginate that can in tandem with other degradable polysaccharides be used in the controlled release of reagents for chemical assays. By modification of alginate with certain solubilized ionic salts, various degrees of porosity can be generated in the hydrogel. The porous hydrogel may be used as a filtering device. By addition of solutions of electrolytes and oxides the conductivity of the alginate hydrogel can be increased or decreased, respectively. The porous alginate can incorporate a reagent used for the determination of an analyte. The reagent releases on exposure to the reacting solution. The porous alginate can be used as a hydrogel core for a series of coatings of reagents mixed with various molecular weight polysaccharides. These are designed to release the reagents serially from the outer layer to subsequent interior and finally inner hydrogel core layers, based on the decreasing solubility of each polysaccharide. If the analyte is sensitive to dilution, the selected polysaccharide(s) can be solubilized with the specific affiliated lyase. The catalytic mechanism, via the breaking of glycosidic bonds in the polysaccharides increases the solubility with negligible dilution of the analyte sample.

Alginate hydrogel has two affiliated lyases. This enables implantation of toxic or catalytic materials in the hydrogel, minimizing exposure of technical personnel while permitting recycling and recovery of the catalytic material at an appropriate facility.

Alginate, once gelled does not solubilize on further dilution with the same solvent (in contrast to the other mentioned high molecular weight polysaccharides that dissolve in excess solvent). Alginate can have gel setting times of 1-20 minutes and this is a function of the salt used, the dilution factor and set temperature. For the purpose of designing alginate of varying porosity a longer setting time of at least 10 minutes is desirable. To achieve the desired setting time a dilution factor of 1:5 parts (dry weight of alginate plus added reagents to solvent weight of distilled water). This enabled homogeneous mixing of the gel during the workable stage to a smoother consistency and time for pipetting of various volume droplets (in these experiments 50-300 microliter beads of initial volume were produced) onto Teflon baking sheets or wax paper prior to being fully set. This mixing and droplet (bead) forming process can be easily automated with existing industry equipment. Alternately larger gel samples were prepared by placing the samples in 1 mL or 5 mL pipet tips. Once fully set alginate undergoes syneresis. This is the process that sparked interest in the investigation of alginate for reagent delivery and led to subsequent other discoveries and applications. Syneresis is the expulsion of liquid from the set gel as it undergoes contraction. The gelled droplets sweat.

Figure 2:
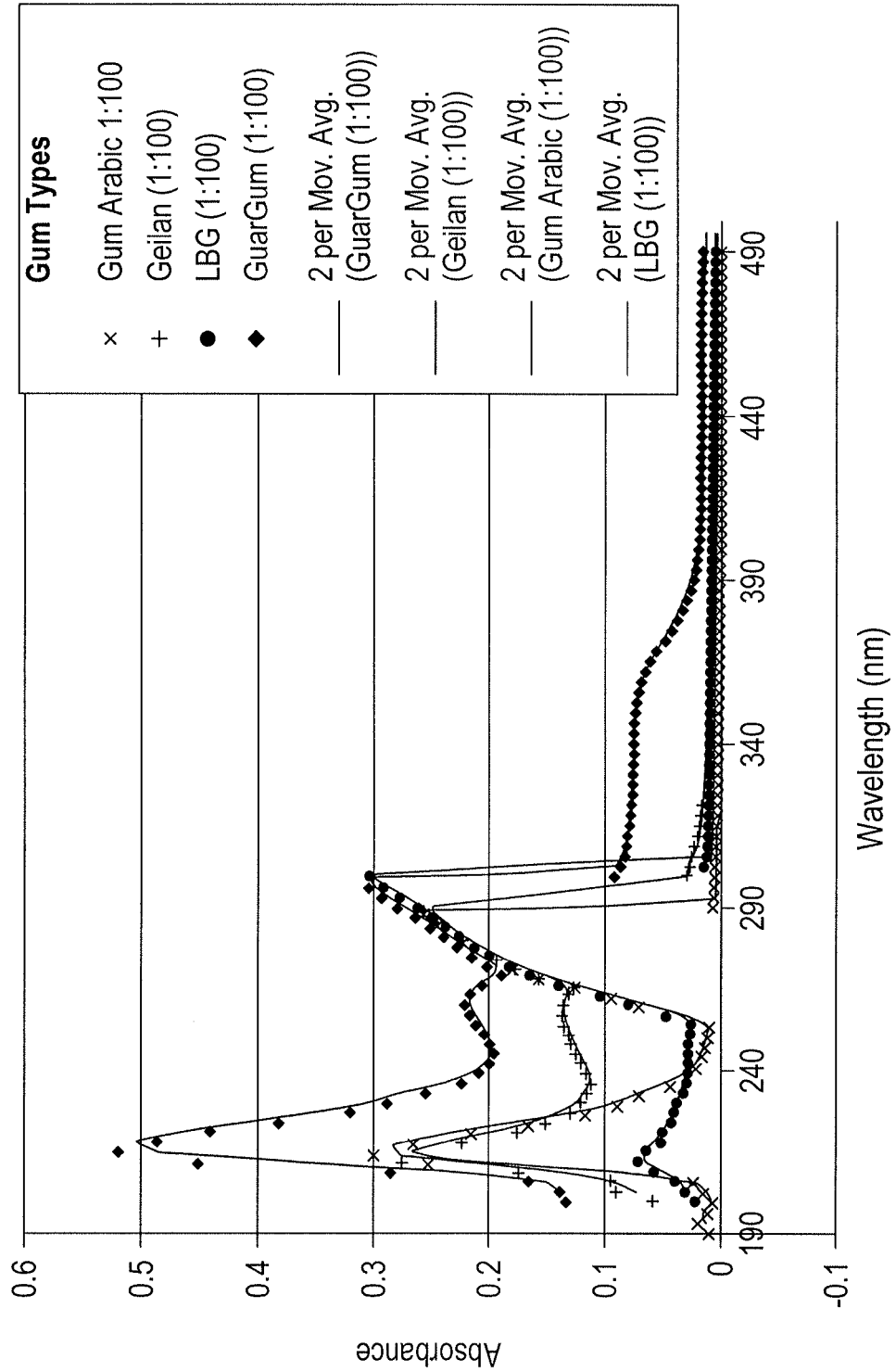
FIG. 2 is a graph showing absorbance versus wavelength of various gel and gum materials.

The first experiment performed was the coating of prepared beads using the syneresized liquid from the bead to adhere a dry chemical reagent. It was found that further evaporative loss could be prevented by dusting the reagent covered bead with confectioner sugar. Further investigation demonstrated that other gum types were more suitable and stable as a coating seal material. These included, but are not limited to, gum arabic, locust bean gum, guar gum, carrageenan and gellan. UV Spectrophotometric analysis, a graph of which is shown in FIG. 2, of these polysaccharides showed that the absorbance of these species was below 310 nanometers (nm) (in all samples except guar gum that continued to show slight absorbance between 0.075 decreasing to 0.015 at 390 nm) and therefore insignificant and well below the range of observation for the testing of drinking and waste water quality—the first target applications.

A second series of experiments were performed that demonstrated that a second reagent could be added to the first reagent over the alginate core, by mixing it in gellan and applying by a rolling process to the existing bead. This could be done in a manufacturing process through a spray coating and drying process.

A third series of experiments demonstrated that by approaching the limit of gelation of alginate (higher ionic strength addition), in addition to protracting the setup time, the alginate had greater porosity. By mixing the added salts (source of cations) with high molecular weight dyes—specifically Allure (a red dye) and Blue Dextran at these higher ionic strength solutions, it was found that the alginate matrix at the selected ionic strength did not retain these dyes. However in samples mixed with lower concentration of salt, these dyes were entrapped within the resulting alginate hydrogel. The ionic strength desired to obtain high pore content were able to be visually determined by the included indicator dye. When alginate at the specific ionic strength was mixed with blue or red dye to produce a pale colored hydrogel, a highly porous gel matrix was indicated when a concentrated dye exudate appeared during syneresis. If the ionic strength was lower, the gels retained the pale coloration as the dye was entrapped within the gel. Thus, to produce higher porosity of the alginate was experimentally determined to be at the limit that maintained larger gel pores capable of exuding the bulky dye molecules. Upon soaking in solvent the entrapped dye in the lower ionic strength gel mixtures eventually diffused from the colloid indicating that the retention time of the dye was very protracted due to smaller pore size.

Figure 3:
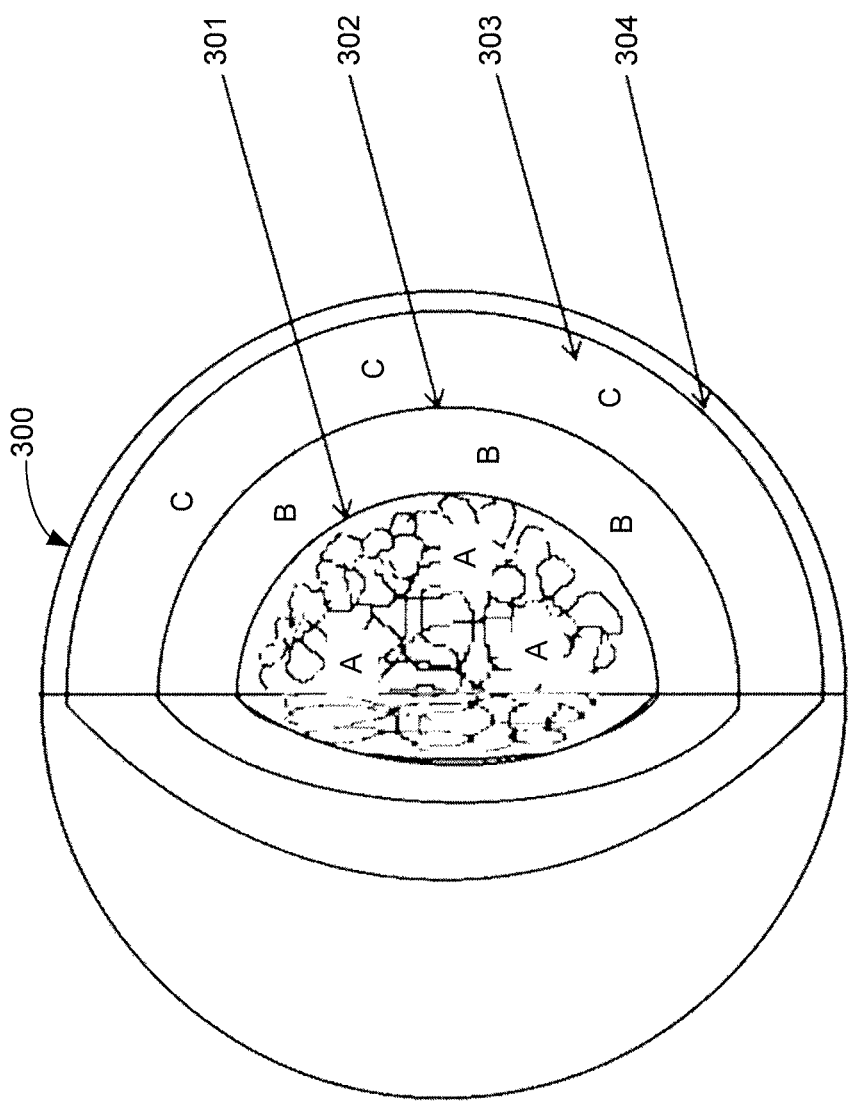
FIG. 3 depicts a prepared bead for reagent assay in accordance with an embodiment of the present disclosure.
Figure 4:
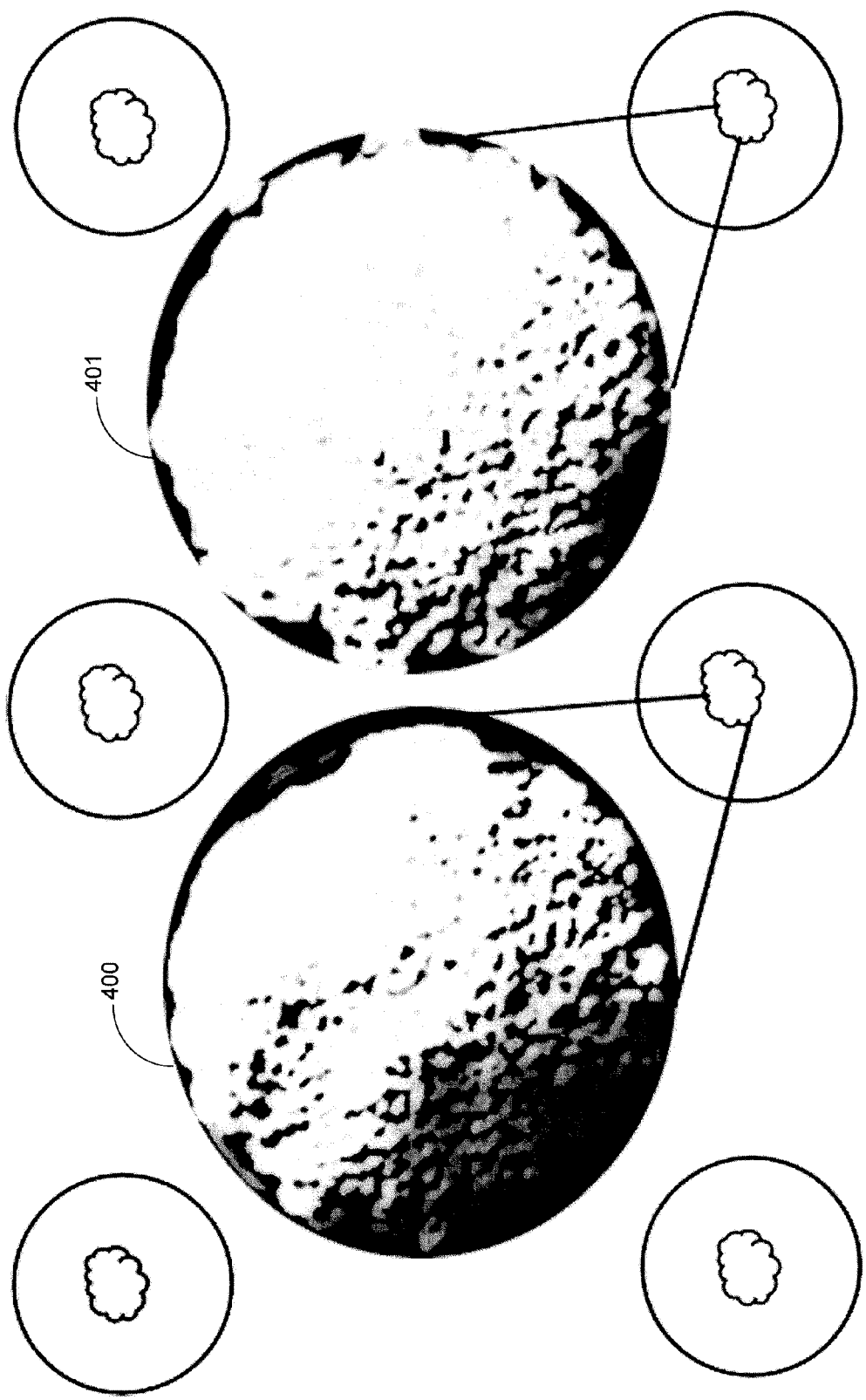
FIG. 4 depicts enhanced porosity of alginate in alginate samples.

Disclosed is a method of chemically modifying the porosity as depicted in FIG. 4 and that can in tandem with other degradable polysaccharides be used in the controlled release of reagents for chemical assays as shown in FIG. 3. By modification of alginate with certain solubilized ionic salts, various degrees of porosity can be generated in the hydrogel. The hydrogel formulation contained 92% to 98% weight to total weight (% w/w) of dry sodium alginate with up to 8% added salt. Note that the percentages of substances is for exemplary purposes and other percentages of substances may be used in other embodiments. This range reflects the use of two product sources of sodium alginate. One source is a prosthetic grade sodium alginate, a product from harvested brown seaweed (kelp), and the other source was Reagent Grade Alginic Acid Sodium Salt by ACROS (CAS 9005-38-3-Lot A0339825). A matrix screen was conducted with various additions of sodium, calcium, or potassium salts at ambient temperature (68° F./20° C.) or slightly below ambient temperature. The result of the matrix screen indicated that the potassium cation from potassium chloride (KCl from Fisher Scientific S25484A Lot 4AH1307-3125A) and potassium iodide (KI from ACROS CAS 7681-11-0 Lot B0137921) produced large pores that retained uniformity. The amount of the potassium iodide required for the pore formation was 4% w/w when using the prosthetic grade alginate as depicted in FIGS. 4. 400 and 401 (repeat sampling) that shows uniformity in the matrix screen. The ACROS product also produced uniform pore formation of comparable size at 7.5% w/w. Greater addition of the selected salts were needed when using the ACROS product or Fisher product, presumably as a result of product higher purity. The alginate once gelled remained stable and pliable for several months when stored in a container of minimal air volume to maintain humidity level. This enables storage of prepared beads.

FIG. 3 depicts a prepared bead 300 in accordance with an embodiment of the present disclosure. The prepared bead 300 comprises an inner porous alginate core 301 created by modification of alginate hydrogel, as described further herein, and containing a first reagent A. Note that the identification of reagent A in the alginate core 301 is for exemplary purposes only, and greater or fewer occurrences of reagent A are possible and probable. The prepared bead 300 shows the porous core on which additional polysaccharide plus reagent layers may be added comprising outwardly extending layers as shown in FIG. 3. The outer layer 304 is solely a polysaccharide used as a seal.

As noted hereinabove, by modification of alginate hydrogel via inclusion of various percentages by weight (hereinafter "% w/w") of sodium, calcium and potassium salts that introduce porosity within the hydrogel, an analyte assay reagent may be incorporated within these pores and subsequent polysaccharide coating layers and be released on exposure to aqueous solution or solvent. Note that the hydrogel formulation contains 92% to 98% weight to total weight (% w/w) of dry prosthetic grade sodium alginate. The prepared salts of alginic acid (sodium alginate, potassium alginate or ammonium alginate) form an irreversible hydrocolloid gel matrix in comparison to the non-water soluble alginic acid. Therefore the prepared salts are the base formulation used in these compositions prior to addition of further salts used to generate the pore formation. Addition of the analytical reagents may be mixed into wet pre-set alginate, adhered to the surface of set alginate, incorporated into dehydrated dried porous alginate in reagent solution under vacuum or tumbled as a dry reagent into dry porous alginate beads.

In accordance with an embodiment of the present disclosure, a serialized timed-release of reagents, e.g., reagents A, B, and C depicted in FIG. 3, can be achieved by encapsulating reagents within and in surrounding layers of a porous hydrogel core, as described hereinabove. As shown, reagents may be layered on the alginate core 301 separated by a series of polysaccharides layers 302 and 303 of successively lower solubility as the layers 302 and 303 move outward from the core. Note that each reagent A, B, and C would be mixed with a gum agent that includes but is not limited to locust bean gum, guar gum, gum arabic, tara gum, xanthan gum, pullulan gum and gellan gum. The molecular weight composition and affiliated solubility of these gums in aqueous solution vary. Reagents are solubilized by exposure to aqueous solution until all of the reagents have reacted in the analyte assay sequence, minimizing the reagent quantities needed, maximizing reaction efficiency and eliminating competing reactions that occur in alternate bulk solution processes. As shown in FIG. 3, the porous core 301 contains the last reagent for release in the analyte process and below the outer polysaccharide seal is the first reagent C to be released. Each of the reagents C, B and A would be released by dissolution of the previous layer.

Figure 6:
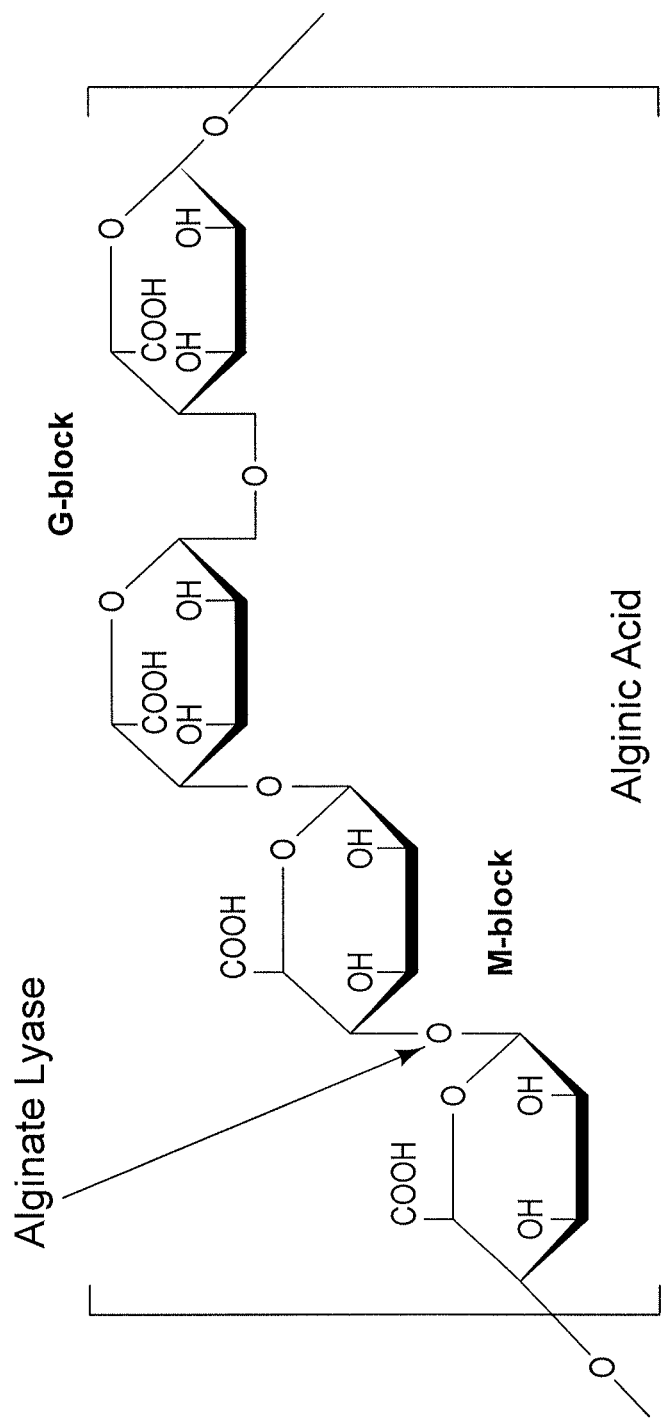
FIG. 6 depicts an alginate lyase.

In one embodiment, use of lyase 600 as shown in FIG. 6 in the assay reduces the amount of solvent (usually water) to dissolve the polysaccharide-reagent containing layers 302-303 shown in FIG. 3. If dilution by aqueous medium of the analyte is problematic, each of the long chain polymer polysaccharide gums selected can be enzymatically cleaved into smaller segments by lyase 600. Note that lyases are specific for cleavage of a particular polysaccharide (e.g: a lyase for gellan would be different than one for alginate). The mechanism of action is usually through cleavage of the glycosidic bond through a β-elimination process. By breaking these long chain polymers into small chains, solubility is enhanced. As a catalytic material, lyase addition (usually by droplet) is a small volume addition. As an enzymatic protein catalyst a spectrophotometric peak will be evident at 235 nm. This UV region is usually below the analyte test region for conventional water or wastewater analysis—however it may interfere with certain biological testing assays centering on 235 nm.

Note that in one embodiment, the porous hydrogel without the inclusion of reagents may be used as a filtering device or size exclusion device in columns, funnels, pipets and microfluidic channels.

Figure 5:
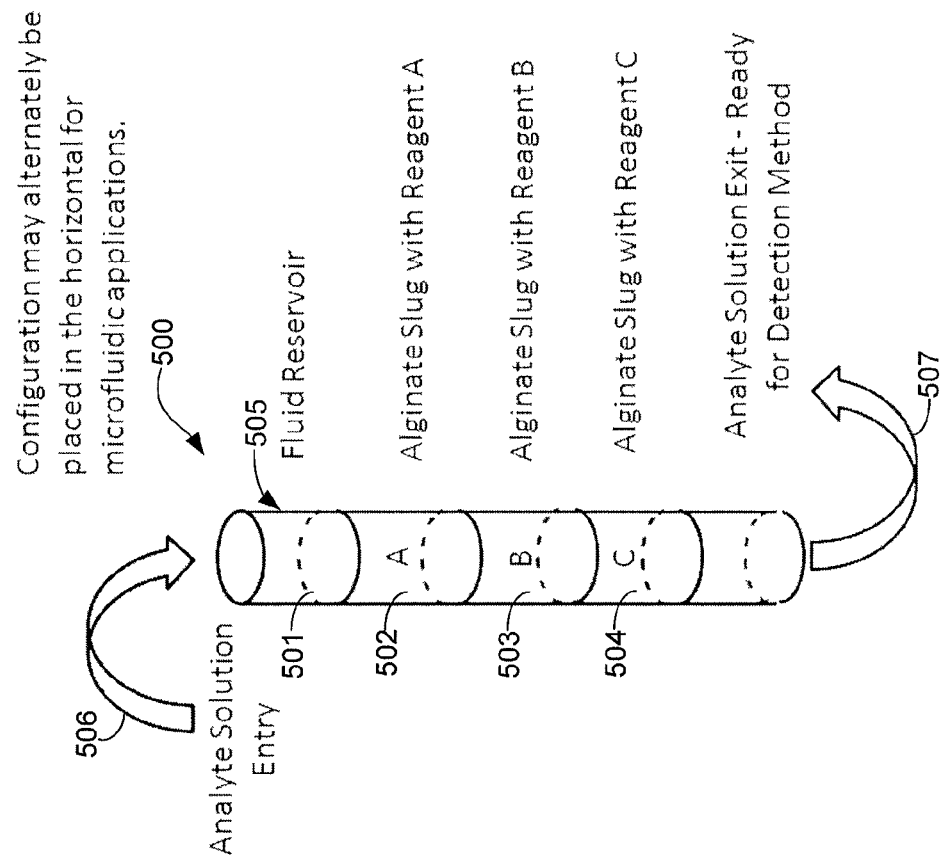
FIG. 5 depicts another reagent assay in accordance with another embodiment of the present disclosure.

FIG. 5 depicts another exemplary reagent assay 500 in accordance with an embodiment of the present disclosure. The reagent assay 500 comprises a container 505, which may be for example an open-ended pipet. In addition, the reagent assay 500 comprises one or more porous alginate plugs. In this regard, the reagent assay 500 comprises porous alginate plugs 502-504.

As noted hereinabove, each porous alginate plug 502-504 is made up of a porous alginate substance. Further, within the porous alginate substances are respective reagents A, B, and C. Note that only a single letter, including A, B, and C, are shown for exemplary purposes depicting the reagent. However, each porous alginate substance includes a myriad of instances of the reagent contained therein.

In use, an analyte solution, depicted by reference arrow 506, is poured into the container 505 in the fluid reservoir 501. From there, the analyte solution 506 travels through the first porous alginate plug 502 reacting with reagent A. Thereafter, the analyte solution 506 travels through porous alginate pulg 503 reacting with reagent B, then through porous alginate plug 504 reacting with reagent C. Once the analyte solution 506 has traveled through each porous alginate plug, the reacted analyte solution, depicted by reference arrow 507, may exit the tube for further analysis.

In such an embodiment, a series of tubular slugs of alginate containing reagents can be aligned and placed in tandem within a cylindrical tube. The analyte can be placed at the opening of the tube and permitted to percolate through each successive slug. The solution exiting the tube (outflow) would then be ready for the detection method for that analyte. This could also be readily adaptable to microfluidic methods where the gelled reagents are placed inline in the microfluidic channels. This enables the sealing of a microfluidic chip with all reagents constrained within an insoluble and immobilized gel. This type of microfluidic chip could function in gravity driven, applied pressure or in sipper mode (pulling of the solution by gentle suction on the outflow port). For utilization of this method in the field, a tube (straw-like) could include the gel slugs with reagents, the analyte, for example a water sample, could be guided gently through the tube (using a syringe bulb) and the sample collected for detection. If the method is colorimetric this could be compared to a color chart.

Note that in one embodiment the porous alginate core 301 (FIG. 3) may be used as a non-dissolving substrate to contain catalytic materials that may be reused or recovered for recycling. This sustainable method also promotes safety in handling. The alginate core is an irreversible hydrocolloid gel. In processes requiring rare or toxic catalyst inclusion, the ability to recover these materials is important. As an example, cadmium beads within a glass column are often used in reduction assays. Cadmium beads could be mixed with porous alginate, confining it for safety within the gel (breakage of a glass column would not cause cadmium spillage as it would remain intact in the hydrogel). In microfluidic applications where reagents are stored on a chip the catalytic material could be extracted via a punch mechanism and recycled. Alginate also has two specific lyases. One breaks the glycosidic bond of an M-block and the other breaks the glycosidic bond of a G-block. Therefore addition of these lyases to alginate, and subsequent disruption of those bonds enables extraction of the cadmium beads on sedimentation or sedimentation-assisted centrifugation.

What is claimed is:

1. A stepwise reagent assay configured for testing of a desired analyte, comprising: an innermost porous core covered with a polysaccharide coating configured for preventing loss of hydration, the innermost porous core containing an innermost reagent configured for reaction with the desired analyte in a created solution; a midmost polysaccharide layer coating the innermost porous core and comprising a midmost reagent configured for reacting with the desired analyte in an initial solution to form the created solution; and an outermost polysaccharide layer coating the midmost polysaccharide layer, the outermost polysaccharide layer configured for sealing moisture within the assay and configured for dissolution when exposed to the initial solution; wherein the desired analyte is contained within the initial solution, the initial solution configured for dissolving the outermost polysaccharide coating, upon dissolution of the outermost polysaccharide coating, the desired analyte reacts with the midmost reagent to form the created solution, and the created solution reacts with the innermost reagent to form a final solution, the final solution providing information related to the inclusion or exclusion of the desired analyte.

2. The reagent assay of claim 1, wherein the innermost porous core is alginate hydrogel.

3. The reagent assay of claim 1, wherein the innermost porous core is gellan.

4. The reagent assay of claim 2, wherein the innermost porous core is created by modification of alginate hydrogel.

5. The reagent assay of claim 4, wherein the modification of the alginate hydrogel is effectuated via inclusion of various percentages by weight of a salt, wherein the salt is selected from the group consisting of sodium salt, calcium salt, magnesium, potassium salt, or salts of other alkali and alkaline earth metals in group 1 and group 2 of the Periodic Table of Elements.

6. The reagent assay of claim 5, wherein the salt introduces porosity within the alginate hydrogel.

7. The reagent assay of claim 6, wherein the alginate hydrogel contains approximately 92% to 98% weight to total weight of a dry prosthetic grade sodium alginate.

8. The reagent assay of claim 1, wherein the innermost reagent is mixed into wet pre-set alginate to form the innermost porous core filled with innermost reagent by degassing, dehydration, mechanical agitation, thermal heating, whereby this incorporation is enabled by filling of vacancies formed by exiting gas bubbles.

9. The reagent assay of claim 1, wherein the innermost reagent is adhered to a surface of set alginate to form the innermost porous core.

10. The reagent assay of claim 1, wherein the innermost reagent is incorporated into dehydrated porous alginate in a solution of the innermost reagent to form the innermost porous core filled with innermost reagent.

11. The reagent assay of claim 1, wherein the innermost reagent is mixed with a hydrogel gum agent.

12. The reagent assay of claim 11, wherein the hydrogel gum agent is selected from a group consisting of alginate, gellan gum, locust bean gum, guar gum, gum Arabic, tara gum, and xanthan gum.

13. The reagent assay of claim 1, wherein a solubility of the outermost polysaccharide coating is greater than a solubility of the midmost polysaccharide layer and the midmost polysaccharide layer is greater in solubility than the innermost polysaccharide coating and the innermost polysaccharide coating is greater or equal to the solubility of the innermost porous core.

14. The reagent assay of claim 1, wherein the polysaccharide coatings or layers are broken into smaller polymer segments through the use of a protein lyase that catalyzes the breakage of glycosidic bonds between two monomeric components of the polysaccharide and that is specific to that polysaccharide and can be used to enhance solubility of that polysaccharide without solubilizing lower layers.

15. The reagent assay of claim 1, wherein quantities of each of the reagents are minimized in comparison to bulk mixtures, reduces waste disposal of these reagents, efficiency with the desired analyte is maximized, and competing reactions are eliminated or minimized.

16. The reagent assay of claim 1, wherein the initial solution is water, saliva urine, or blood serum.

17. A stepwise reagent assay method configured for testing of a desired analyte, comprising: (a) creating a testing bead comprising: an innermost porous core covered with a polysaccharide coating to prevent loss of hydration, the innermost porous core containing an innermost reagent; a midmost polysaccharide layer containing a midmost reagent, the midmost polysaccharide coating surrounding the innermost porous core; an outermost polysaccharide coating surrounding the midmost polysaccharide layer and providing a hydration seal; (b) dissolving the outermost polysaccharide coating in the initial solution; (c) dissolving the reagent contained within the midmost polysaccharide layer in the initial solution, a first product is created from the reaction of the desired analyte with the midmost reagent, thereby forming a created solution, a second product; (d) dissolving the polysaccharide coating of the innermost porous core to enable reaction of the reagent contained within the innermost core with the created solution to form a the final solution, a third product configured for analyte testing.

18. The reagent assay method of claim 17, wherein the reagent assay is configured to perform a chemical process having additional layers and thus additional intermediates solutions and intermediate products for testing the desired analyte.

19. The reagent assay method of claim 17, wherein the reagent assay is configured to perform a chemical process having additional steps and one or more of the steps may be represented by one or more additional beads in a solution to perform the chemical process.

20. The reagent assay method of claim 17, wherein the creating comprises making the innermost porous core of alginate hydrogel.

21. The reagent assay method of claim 17, wherein the creating comprises making the innermost porous core of gellan.

22. The reagent assay method of claim 21, further comprising making the innermost porous core by modification of alginate hydrogel.

23. The reagent assay method of claim 19, wherein the modification of the alginate hydrogel is effectuated via inclusion of various percentages by weight of a salt selected from the group consisting of sodium salt, calcium salt, magnesium or potassium salt and salts of other alkali and alkaline earth metals in group 1 and group 2 of the Periodic Table of Elements.

24. The reagent assay method of claim 23, further comprising introducing porosity within the alginate hydrogel.

25. The reagent assay method of claim 24, further comprising making the alginate hydrogel such that it contains approximately 92% to 98% weight to total weight of a dry prosthetic grade sodium alginate.

26. The reagent assay method of claim 17, wherein the creating further comprises mixing the innermost reagent into wet pre-set alginate to integrate into the innermost porous core, whereby this incorporation can be achieved by degassing, dehydration, mechanical agitation, or thermal heating of the mixture enabling the reagent to fill vacancies left by exiting gas bubbles.

27. The reagent assay method of claim 17, further comprising adhering the innermost reagent to a surface of set alginate to form the innermost porous core.

28. The reagent assay method of claim 17, further comprising incorporating the innermost reagent into dehydrated porous alginate to form the innermost porous core.

29. The reagent assay method of claim 17, wherein the creating comprises mixing the innermost reagent with a gum agent.

30. The reagent assay method of claim 29, wherein the mixing further comprises mixing with the gum agent which is selected from a group consisting of alginate, gellan gum, locust bean gum, guar gum, gum Arabic, tara gum, xanthan gum.

31. The reagent assay of claim 1, wherein the polysaccharide coatings or layers are broken into smaller polymer segments through the use of a protein lyase that catalyzes the breakage of glycosidic bonds between two monomeric components of the polysaccharide and that is specific to that polysaccharide and can be used to enhance solubility of that polysaccharide without solubilizing lower layers.

32. The reagent assay method of claim 17, further comprising:
   minimizing quantities of each of the included reagents;
   reduces waste disposal of these reagents;
   maximizing reaction efficiency with the desired analyte; and
   eliminating or minimizing competing reactions in comparison to bulk assay methods.

33. The reagent assay method of claim 17, wherein the assay introduces changes in a stepwise manner as each reagent is released from the layers, changing the solution mixture characteristics on each release generating a new product, respectively.

34. The reagent assay method of claim 17, further comprising changing characteristics of the created and/or final solution based upon the midmost and/or innermost reagent, respectively.

35. A reagent assay for securing an unstable analyte for future testing, comprising: the soluble analyte mixed with gellan to create a porous polysaccharide core, the porous core covered with a first polysaccharide coating; wherein the analyte is stabilized in the porous core, wherein the first polysaccharide coating is configured to undergo dissolution such that the analyte will be released for testing.

36. The reagent assay of claim 1, wherein when the polysaccharide layer is not readily soluble in the initial solution or the created solution, further comprising adding one or more protein lyases that are specific for polysaccharides in the polysaccharide layer configured to cleave glycosidic bonds within each polysaccharide to promote dissolution.

* * * * *